US011199120B2

(12) United States Patent
Pachner et al.

(10) Patent No.: US 11,199,120 B2
(45) Date of Patent: Dec. 14, 2021

(54) INFERENTIAL FLOW SENSOR (71) Applicant: Garrett Transportation I Inc., Torrance, CA (US)

(72) Inventors: Daniel Pachner, Prague (CZ); Michael Uchanski, Vevey (CH); Lukas Lansky, Prague (CZ)

(73) Assignee: Garrett Transportation I, Inc., Torrance, CA (US)

(*) Notice: Subject to any disclaimer, the term of this patent is extended or adjusted under 35 U.S.C. 154(b) by 298 days.

(21) Appl. No.: 16/348,497

(22) PCT Filed: Nov. 29, 2016

(86) PCT No.: PCT/US2016/064036
§ 371 (c)(1),
(2) Date: May 8, 2019

(87) PCT Pub. No.: WO2018/101918
PCT Pub. Date: Jun. 7, 2018

(65) Prior Publication Data
US 2019/0271274 A1    Sep. 5, 2019

(51) Int. Cl.
*F01N 11/00* (2006.01)
*F02D 41/00* (2006.01)
(Continued)

(52) U.S. Cl.
CPC ............ *F01N 11/005* (2013.01); *F01N 3/208* (2013.01); *F01N 9/005* (2013.01); *F01N 11/007* (2013.01);
(Continued)

(58) Field of Classification Search
CPC ........ F01N 11/005; F01N 3/208; F01N 9/005; F01N 11/007; F01N 2560/026; F01N 2900/14; F02D 41/0072; F02D 41/1458; F02D 41/1456; F02D 41/2451; F02D 41/2454; F02D 2200/0402; F02D 2200/0406; F02D 2200/0411; F02D 2200/0414; F02D 2200/0418;
(Continued)

(56) References Cited

U.S. PATENT DOCUMENTS 8,700,291 B2 * 4/2014 Herrmann ........... F02D 41/1402
701/108
9,267,452 B2 * 2/2016 Auckenthaler ..... F02D 41/0007
(Continued)

FOREIGN PATENT DOCUMENTS

EP    2339153 A1    6/2011
EP    2853723 A1    1/2015
FR    2992351 A3    12/2013

OTHER PUBLICATIONS

International Search Report and Written Opinion for Application No. PCT/US2016/064036, 4 pages, dated Jul. 19, 2017.

Primary Examiner — Freddie Kirkland, III
(74) Attorney, Agent, or Firm — Seager, Tufte & Wickhem, LLP (57) ABSTRACT A system and an approach for determining various flows in an internal combustion engine, such as an amount of recirculation exhaust gas flow through a controlled valve and a fresh air mass flow to an intake of an engine. Also, among the sensors accommodated in the system, is an inexpensive but slow-responding lambda sensor in the exhaust stream.

14 Claims, 2 Drawing Sheets (51) Int. Cl.
*F02D 41/14* (2006.01)
*F01N 3/20* (2006.01)
*F01N 9/00* (2006.01)
*F02M 35/10* (2006.01)
*G01N 33/00* (2006.01)
*F02D 41/24* (2006.01)

(52) U.S. Cl.
CPC ..... *F02D 41/0072* (2013.01); *F02D 41/1458* (2013.01); *F02M 35/1038* (2013.01); *G01N 33/0037* (2013.01); *F01N 2560/026* (2013.01); *F01N 2900/14* (2013.01); *F02D 41/1456* (2013.01); *F02D 41/2451* (2013.01); *F02D 41/2454* (2013.01); *F02D 2200/0402* (2013.01); *F02D 2200/0406* (2013.01); *F02D 2200/0411* (2013.01); *F02D 2200/0414* (2013.01); *F02D 2200/0418* (2013.01); *Y02A 50/20* (2018.01); *Y02T 10/40* (2013.01)

(58) Field of Classification Search
CPC ........... F02M 35/1038; G01N 33/0037; Y02A 50/20; Y02T 10/40
See application file for complete search history.

(56) References Cited

U.S. PATENT DOCUMENTS

| | | | |
|---|---|---|---|
| 10,309,287 B2* | 6/2019 | Pachner | F01N 9/005 |
| 2010/0131181 A1 | 5/2010 | Herrmann | |
| 2012/0325188 A1* | 12/2012 | Auckenthaler | F02D 41/2451 123/568.21 |

* cited by examiner

INFERENTIAL FLOW SENSOR

BACKGROUND

The present disclosure pertains to sensors, engines, and particularly to components related to emissions reduction of the engines.

SUMMARY

The disclosure reveals a system and an approach for determining various flows in an internal combustion engine, such as an amount of recirculation exhaust gas flow through a controlled valve and a fresh air mass flow to an intake of an engine. Also, among the sensors accommodated in the system, is an inexpensive but slow responding lambda sensor in the exhaust stream.

DESCRIPTION

The present system and approach may incorporate one or more processors, computers, controllers, user interfaces, wireless and/or wire connections, and/or the like, in an implementation described and/or shown herein.

This description may provide one or more illustrative and specific examples or ways of implementing the present system and approach. There may be numerous other examples or ways of implementing the system and approach.

Aspects of the system or approach may be described in terms of symbols in the drawing. Symbols may have virtually any shape (e.g., a block) and may designate hardware, objects, components, activities, states, steps, procedures, and other items.

The mass flows in the turbocharged combustion engine, particularly the fresh air mass flow and the exhaust gas recirculation (EGR) mass flow, are important control parameters which need to be carefully controlled.

The fresh air mass flow determines the oxygen availability for the fuel combustion. It may be noted that oxygen unavailability may lead to incomplete combustion and generation of soot particles which can either be observed as tailpipe smoke or which may clog the particulate filter. In combustion engines, both gasoline and diesel, the fresh air flow usually needs to be controlled to a desired ratio to the fuel mass flow.

The EGR mass flow determines the portion of inert three atomic gases $H_2O$ and $CO_2$ in the gas charged to cylinders. An inert content dissolves the oxygen and increase the thermal capacity of the charged gas. The increased thermal capacity and lowered oxygen availability of the charged gas may both lead to lower peak temperatures in a cylinder which reduces formation of nitrogen oxides NO and $NO_2$ (i.e., $NO_x$). The mass of these harmful oxides produced by engines may be regulated by emission limits.

Although the mass flows are important control parameters, they may not always be easily measured with a sufficient degree of accuracy, robustness, and reliability. Also a cost of such physical sensors may be considered high. The air mass flow sensors based on principles such as hot-film sensors (HFS), or EGR mass flow sensors based on a Venturi tube principle, can be associated with significant costs, calibration efforts, and reliability issues. It may be therefore practical to calculate the mass flows from other physical quantities which can be measured easier, especially if sensors for those physical quantities are already present in the system because of other control or monitoring functions. It may be noted that the physical flow sensors can either be replaced by the calculated values or the calculated values may be used to improve the physical sensor signal, or may be used to diagnose failures of those physical flow sensors.

The quantities which can be measured accurately and with significantly better reliability than mass flows are the intake side pressures and temperatures, which are temperatures and pressures between the air intake up to the cylinder. The turbo-speed, and oxygen content, namely, oxygen mole fraction in the exhaust gas can also be measured reliably. It may be noted that measuring pressures and temperatures on the exhaust side may be significantly more difficult due to harsh conditions there that can include high temperatures, pressure pulsations, and combustion products such as water considering that water may freeze in winter, aggressive Sulphur compounds, and deposits of soot and oil residues.

A virtual mass flow sensor may calculate the fresh air mass flow, the EGR mass flow, or both, based on those other physical sensors which may be available easier. These calculations may be based on models of the engine components and equations, which describe how the components are coupled and how they interact.

Figure 1:
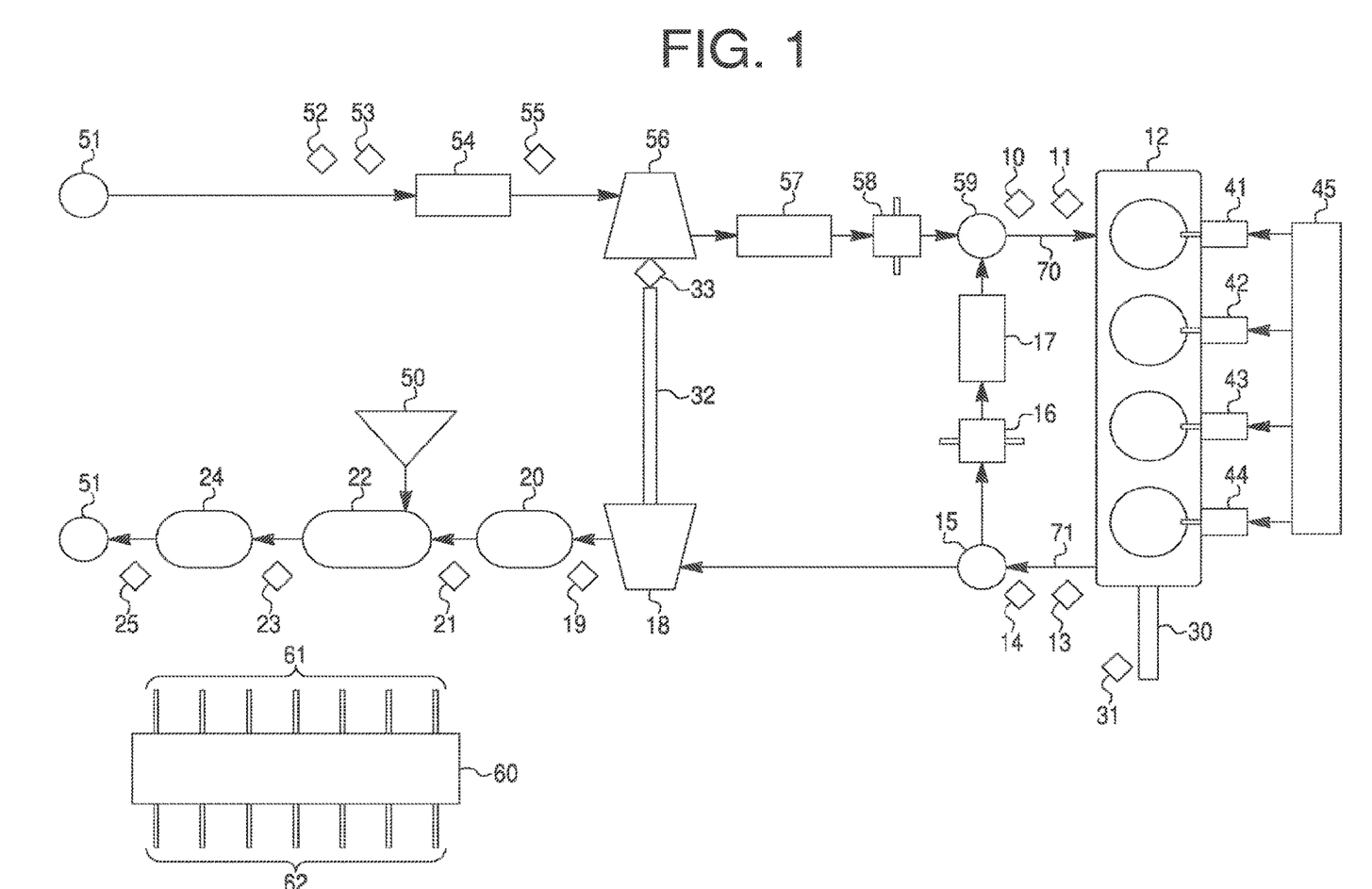
FIG. 1 is a diagram of a turbocharged diesel engine.

FIG. 1 is a diagram of a turbocharged diesel engine. A system of the gas flows in the turbocharged diesel engine with a high pressure EGR valve is shown in the diagram. The diagram shows layout of an internal combustion engine 12 and its peripheral components related to air and fuel supply. Engine 12 may have an intake manifold 70 and an exhaust duct or manifold 71. Intake pressure ($p_2$) and temperature ($T_2$) may be detected with a pressure sensor 10 and a temperature sensor 11, respectively. Exhaust pressure ($p_3$) and temperature ($T_3$) may be detected with a pressure sensor 13 and a temperature sensor 14, respectively. However, most production engines will not necessarily be equipped with sensors 13 and 14 due to a difficulty with sensors placed on the exhaust side.

In operation, air may come in from an ambient environment 51 at an input pressure ($p_1$) and temperature ($T_1$) as indicated by sensors 52 and 53, respectively, positioned before the air filter 54. The air may be compressed by a compressor 56 and flow to a mixing point or plenum 59. Since air becomes hotter when compressed, an engine charge air cooler (CAC) 57 may be used to reduce compressed air temperature. A throttle 58 may be placed downstream of compressor 56 in order to control the pressure in intake manifold 70.

Some exhaust gas may be fed from exhaust manifold 71 through a splitter 15 and through an EGR valve 16 and out of valve through a cooler 17 to the mixing point or plenum 59 where charged air from the compressor 56 and exhaust gas from EGR valve 16 meet. EGR valve 16 may control an amount of EGR gas to plenum 59. Exhaust gas at an input of EGR valve 16 may have a pressure $p_3$ and a temperature $T_3$. Exhaust gas that is not directed toward EGR valve 16 may go to drive a turbine 18 which turns a shaft 32 at N rotations per unit of time or a rate of angular movement omega ($\omega$) as indicated by a sensor 33. Shaft 32 may drive compressor 56 that outputs the compressed air.

The exhaust gas can pass through a number of aftertreatment devices removing harmful compounds. Firstly, the gas may be passing the diesel particulate filter (DPF) 20 to trap soot particles which may be later burned using just the exhaust heat (passive regeneration) or using an extra diesel fuel injector located at the filter inlet (active regeneration). Some diesel engines may also use a diesel oxidation catalyst (DOC, not shown). Then the gas may be treated in a selective catalyst reduction (SCR) device 22 where most of the nitrogen oxides may be converted into harmless diatomic nitrogen using urea injected by the dosing system 50. In order to control the amount of urea used, SCR device 22 may be equipped with inlet and outlet NOx sensors 21 and 23 which may also provide additional information of the oxygen concentration in the exhaust gas. SCR device 22 may use ammonia created from the urea as a reducing agent to reduce the nitrogen oxides. The excess ammonia which may pass unreacted from SCR 22 as a result of urea overdosing may be removed in the ammonia slip catalyst (AMOX) 24.

Engine 12 cylinders may also be a recipient of fuel via a line or tube 45 to fuel injectors 41, 42, 43 and 44. The fuel from injectors 41, 42, 43 and 44 may mix with the air and EGR gas to the cylinders of engine 12 for combustion to move the pistons and turn the crankshaft for a mechanical rotational output at a shaft 30. Engine speed may be measured by a sensor 31 at shaft 30. Other approaches may be used for measuring engine speed. A lambda or oxygen sensor 19 may be situated in an exhaust duct where an exhaust stream may flow such as, for example, after turbine 18, after DPF 20 as sensor 21, after SCR 22 as sensor 23, after AMOX 24 as sensor 25, or there may be several lambda sensors at several locations, simultaneously. The lambda sensor may be combined with a NOx sensor.

Some acronyms that may be used relative to engine aftertreatment technology may incorporate SCR (selective catalytic reduction), SCRF (SCR on filter), DPF (diesel particulate filter), DOC (diesel oxidation catalyst), LNT (lean NOx trap), and PNA (passive NOx adsorber).

The exhaust stream may mean turbine-out, DOC-out, DPF-out, SCR-in, SCR-out, and even tailpipe-out. Though the oxygen content does not necessarily change significantly in the exhaust stream, it may be affected by some of the oxidations in the aftertreatment devices. Exhaust configurations may consist of, for example, turbine-DOC-DPF-SCR and turbine-PNA/LNT/DOC+SCRF+SCR. The lambda or oxygen sensor may be situated virtually anywhere.

A processor 60 may receive inputs 61 from one or more sensors of sensors 52, 53, 33, 10, 11, 13, 14, 19, 21, 23, 25, via wire or wireless connections. An output 62 from processor 60 may be used for controlling EGR valve 16 or for controlling the throttle 58. Other components, such as coolers 57 and 17, variable geometry of turbine 18 or turbine waste gate, and injectors 41, 42, 43 and 44, may be controlled by outputs 62 from processor 60.

An engine configuration, such as the one in FIG. 1, together with mathematical models of the individual elements in the configuration, may define a set of equations from which the sought mass flow values can be solved. In particular, the mass conservation law in the engine configuration of FIG. 1 may define that the fresh air mass flow equals turbine mass flow minus fuel mass flow, the EGR mass flow equals charged gas flow minus fresh air mass flow.

The equations may hold at any time up to small and negligible dynamic inaccuracies caused by mass accumulation in the intake and exhaust manifolds. It may be noted that from these equations the sought fresh air mass flow and sought EGR mass flow may be calculated indirectly by first calculating the charged gas mass flow $\dot{m}_{ch}$, the turbine mass flow $\dot{m}_t$ and the fuel mass flow $\dot{m}_f$, and calculating the fresh air flow $\dot{m}_a$ and EGR mass flow $\dot{m}_{EGR}$ in a second step. In the next possible ways how fuel, turbine, and charged gas mass flows can be calculated may be noted.

The fuel mass flow $\dot{m}_f$ may virtually always be calculated from the fuel injection quantity per cylinder stroke $q_f$ [mg/cyl/stroke], which may be known to the processor 60; also known is engine speed $N_e$ [rpm], and considering a four stroke engine with $N_{cyl}$ cylinders the fuel mass flow [kg/s] may be indicated by:

$$\dot{m}_f = N_{cyl} \frac{10^{-6}}{120} q_f N_e.$$

The charged gas mass flow $\dot{m}_{ch}$ [kg/s] may be expressed from engine rotational speed $N_e$ [rpm], the engine displacement volume $V_d$ [l], the intake manifold pressure $p_2$ [kPa] and temperature $T_2$ [K], the specific gas constant of the charged gas R [J/kg/K], and the volumetric efficiency parameter $\eta_{vol}$ [–] that is a property of the engine and may depend on engine speed as well as other parameters such as the engine compression ratio, and the exhaust and intake pressures in view of:

$$\dot{m}_{ch} = \frac{1}{120} \eta_{vol}(N_e) V_d \frac{p_2}{T_2 R} N_e.$$

The turbine mass flow $\dot{m}_t$ [kg/s] may be calculated from the turbine inlet pressure $p_3$, turbine outlet pressure $p_4$, turbine inlet temperature $T_3$, and turbine speed $N_t$. Some turbines may have control parameters such as variable geometry or a waste gate. The basis for this calculation may be an experimental turbine map $M_t$ ($N_t$, $p_{30}/p_4$), which defines the turbine mass flow rate for fixed reference inlet pressure $p_{30}$ and temperature $T_{30}$. Using such turbine map, the turbine mass flow $\dot{m}_t$ may be calculated for any inlet pressure $p_3$ and temperature values $T_3$, $$\dot{m}_t = M_t(N_t\sqrt{T_3/T_{30}}, p_3/p_4) p_3/p_{30}\sqrt{T_{30}/T_3}.$$

The above calculation of $m_t$ requires the values $p_3$, $p_4$, $T_3$ which are usually not sensed. However, other similar equations describing the model components can be added to define these values from available signals. The $T_3$ temperature may be estimated modeling the combustion, heat transfer and gas expansion processes in the cylinder. The post turbine pressure $p_4$ may be expressed considering a model of the flow restriction of the post turbine elements. It is virtually always possible to add equations to calculate the rough mass flows from signals known to processor 60. Engines with double stage turbochargers may have two turbines in a cascade. Maps of both turbines may be then used in the calculations.

The EGR mass flow $\dot{m}_{EGR}$ may be calculated from the following orifice equation, $$\dot{m}_{EGR} = \frac{p_3}{\sqrt{T_3}} \Psi\left(\frac{p_3}{p_2}, u_{EGR}\right) \text{ [kg/s]},$$

where $\Psi$ is a flow function that can be calibrated for a specific valve used, $p_3$, $T_3$ is pressure and temperature before the EGR valve in the exhaust duct, $p_2$ is pressure after the EGR valve in the intake manifold, and $u_{EGR}$ is a valve position opening angle or valve opening area.

The calculated fuel mass flow, the charge mass flow, the turbine mass flow and EGR mass flow may then be used to calculate the fresh air mass flow, and the EGR mass flow based on the mass conservation in the engine. The fact that EGR mass flow is both an input and output to these calculations is not necessarily contradictory. The EGR valve mass flow value defined by the valve characteristics may be corrected and made more accurate in the process when the mutual correlations between the flows are used.

The calculation may result in "fast" but possible offset estimates based on the model. A fast estimate means that there is no noticeable delay in the flow estimates relative to the true flow value. At the same time, the flow estimates may often be offset because the turbine characteristics, volumetric efficiency and valve flow function or valve cross section, as well as other properties, are never known accurately, and they may be subject to random changes or drifts during the vehicle life.

One distinctive feature of the invention may be how a lambda sensor is used to remove the offset from "fast" mass flow estimates that are based on a turbine model, EGR valve model, and engine volumetric efficiency model, and possibly other models. A lambda sensor, virtually located anywhere in the exhaust gas stream, may be used to correct the flow estimates reducing the offset. The lambda sensors may sense the oxygen mole fraction $O_2$ (e.g., oxygen content of exhaust gas) which is related to the fresh air mass flow and fuel mass flow. An exact relationship depends on the fuel composition and specific air humidity $H_s$ (water mass fraction in the air). As an example, the following relationship may be derived for fuel composition $C_{12}H_{23}$, $$\dot{m}_a = \frac{\dot{m}_f(3.065 + 0.992 O_2)}{0.21(1 - H_s) - O_2(1 + 0.602 H_s)}.$$

The above equation may define a way in how the fresh air mass flow $\dot{m}_a$ can be calculated from the lambda sensor; or from exhaust gas $O_2$ mole fraction, which was calculated from a lambda sensor output. However, it may be noted that such calculation may lead to a poor air flow estimate in numerous situations for the following reasons: 1) The lambda sensor output may be unavailable until it reaches sufficient temperature; 2) The denominator of the above formula is small and approaching zero for oxygen mole fractions close to 0.21 (that of dry fresh air), and the result of division may then have very large relative error due to usually not accurately known, or completely unknown, air humidity and due to small but nonzero lambda sensor error; 3) The lambda sensor placed between or after the aftertreatment devices may further increase the error because being affected by oxidation reactions in the devices such as soot oxidation in the DPF; and 4) The lambda sensor can have significant delay up to 3 seconds and the $\dot{m}_a$ calculations may thus not be necessarily accurate during non-steady state operation of the engine. For these reasons, the $\dot{m}_a$ usually cannot be calculated from lambda directly at least when any of the above items (1-4) may play a role or when the lambda sensor is a low grade slow sensor.

Figure 2:
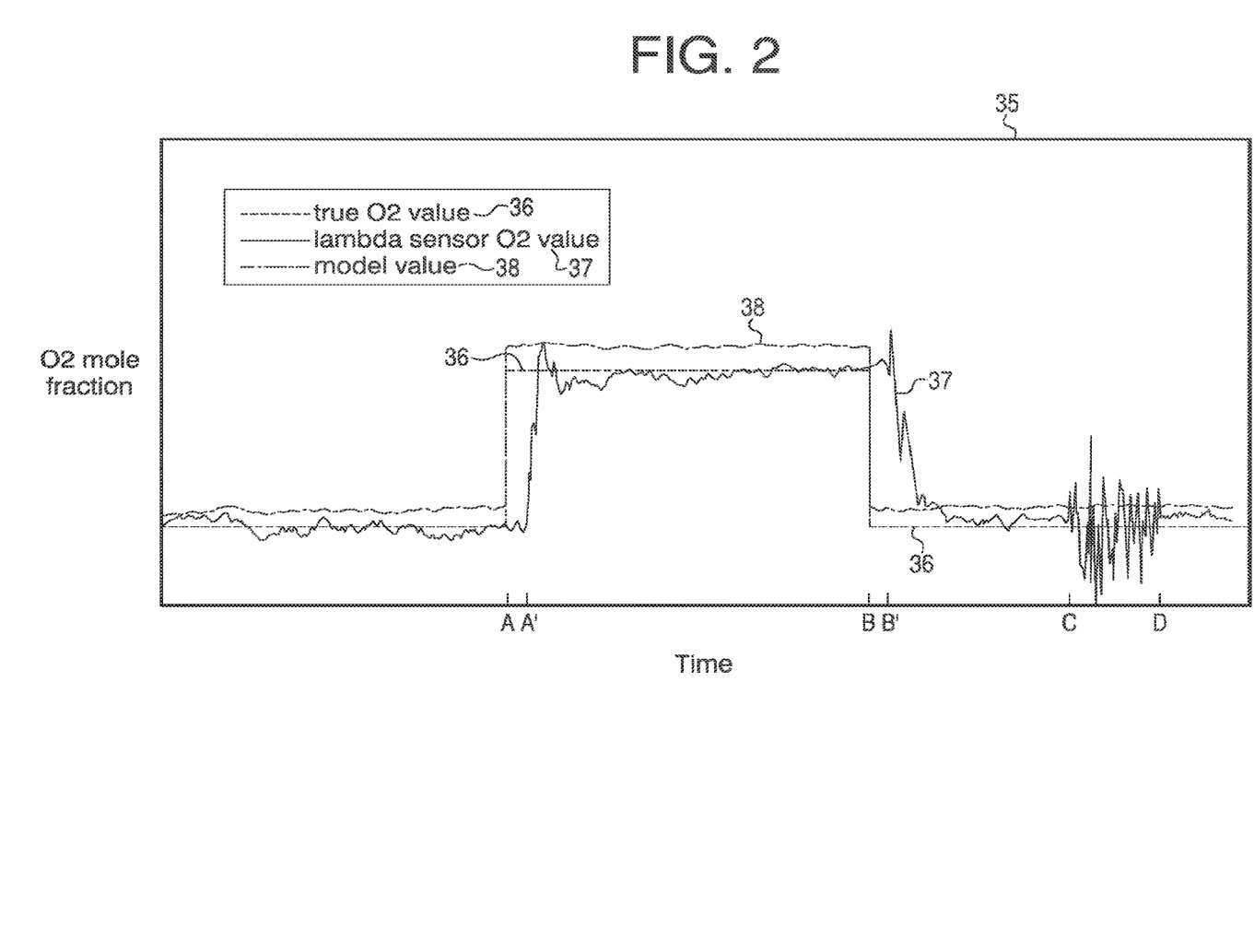
FIG. 2 is a diagram of a lambda sensor behavior graph.

FIG. 2 is a diagram of a lambda sensor behavior graph 35. A possible behavior of the $O_2$ mole fraction derived from lambda sensor signal 37 compared to the theoretical true $O_2$ value 36 and also value 38 calculated from the model equations is in graph 35. It may be noted that when the true $O_2$ value 36 changes at point A or B, the model may be able to predict the change without noticeable delay. However, the model predicted value 38 may be slightly offset for reasons explained before. The $O_2$ value 37 derived from the lambda signal will usually not be offset, or at least the offset will be smaller. However, it may take the lambda sensor (value 37) some time, A-A' or B-B', to reach the true $O_2$ value 36. Also, lambda sensor signal 37 may be noisy and difficult to interpret during transient periods between A-A' and B-B'. Moreover, lambda signal 37 may be affected by other processes, e.g., soot oxidations, and signal 37 may be sometimes temporarily inaccurate like between C and D.

A particular feature of the disclosure is an approach of calculating the theoretical "fast" lambda value 38 from the fuel mass flow, EGR mass flow and turbine mass flow estimates, which are not delayed but may be possibly offset. A lambda value 37 (having a dynamic delay) may be considered in a correction of flow estimates. The correction may slowly adjust the EGR valve and turbine model parameters to match the sensed lambda during more or less steady operation of the engine. The correction may be stronger or correction process may be faster when the lambda sensor operates in the favorable conditions and the lambda signal is steady. The correction may be almost none when the lambda sensor possibly operates in unfavorable conditions or during transient. The correction may be based on calculated sensitivities of the lambda with respect to the adjusted parameters. This sensitivity calculation may involve lambda sensor model, including a dynamic model of the sensor delay, such as lambda sensor time constant and dead time. The correction process may be disengaged during periods of time the lambda not available, e.g., because the lambda sensor has not yet reached the working temperature after cold start. It may be noted that the disclosed approach may still be providing valid flow estimates although the offset may not be fully corrected during these periods. Also considered in the correction may be a relationship between an $O_2$ mole fraction (i.e., a quantity sensed by the lambda sensor) and the air and fuel flows, and how this relationship may be affected by possibly uncertain air humidity.

Various approaches may be noted in the following text. An estimation approach may incorporate calculating fast but possibly offset EGR and air flow estimates using an intake manifold pressure sensor, and temperature sensors if available, turbocharger-speed sensor if available, as well as other available sensors, and finally correcting the offset of these estimates using a lambda sensor signal.

By fast but possibly offset estimates may mean that the flow estimates do not necessarily have any noticeable delay with respect to the true flows but they can be offset systematically because of parameter variations during a vehicle lifetime such as, for example, slow changes in the valve characteristics caused by fouling or soot deposits, or degradation of the turbocharger efficiency. By using the lambda signal, the offset may be removed.

An estimation approach may incorporate calculating fast but possibly an offset EGR and air flows combining EGR valve and turbine(s) plus post turbine elements (e.g., aftertreatment) mass flow models based on sensed or estimated inlet conditions $p_3$, and $T_3$, and making use of a turbo-speed sensor 33 if such turbo-speed sensor is available, which may parameterize the turbine mass flow model. For engines with two or more turbines, the approach may be generalized by treating the cascade of turbines almost as the single turbine.

An estimation approach may incorporate calculating fast but possibly offset EGR and air flows by combining the EGR valve and turbine(s) plus post turbine elements (e.g., aftertreatment) mass flow models where the relative contributions of the EGR valve and turbine(s) plus post turbine elements flow models are changed dynamically reflecting a variability of the accuracies of the flow models which may depend on current pressure ratios. An approach may incorporate estimating $T_3$ using a simplified combustion process model and estimating $p_3$ using a turbocharger model.

An estimation approach may combine a dynamically correct (fast) but possibly offset EGR and air flow estimates with a lambda signal to remove the steady-state offset during periods of time lambda signal is healthy and making use of low frequency component of the lambda signal instead of converting the lambda signal to the air mass flow directly.

An approach may incorporate combining the fast but possibly offset flow estimates with a slow lambda signal using a lambda sensor dynamic model (e.g., a transfer function modelling the lambda sensor dynamics, sensor time constant or interval for an unknown or randomly varying sensor time constant, and sensor dead time, or interval for unknown or randomly varying sensor dead time, or similar statistical, probabilistic, or interval sensor models).

An approach may incorporate adjusting the turbine efficiency, EGR valve flow functions, or other model properties to match the $O_2$ mole fraction sensed by lambda sensor in a steady-state.

A lambda sensor in the noted approaches of the present system may have performance specifications of delay ranging between 1 and 3 seconds depending on the flow velocity and gas parameters, and accuracy often worse than 2 percent. A greater part of the sensor inaccuracy may not necessarily be a property of the lambda sensor but due to additional processes in the system in the aftertreatment. The lambda sensors located in the aftertreatment may be partly affected by chemical reactions in the aftertreatment, some of which may change the oxygen mole fraction to certain degree. This may further decrease the accuracy of the air flow calculation from these sensors. Such a signal may be regarded as poor compared to many typical lambda sensors which may have performance accuracy specifications 2 percent or better. Although such lambda signals may be inappropriate for direct conversion to the air mass flow signal, they may be used to adjust the uncertain or drifting model parameters. Such lambdas located in the in the aftertreatment may be a quite inexpensive solution for the purpose of inferential sensing because they may already be installed for the purposes of aftertreatment control, e.g., urea dosing control, and they may be reused by the inferential sensor.

A distinctive feature of the proposed inferential sensing approach may use the lambda signal for a purpose of model parameters adaptations, e.g., to detect random changes in the system parameters over the vehicle lifetime. At the same time, lambda is not necessarily used to calculate the air flow directly. Therefore, the $O_2$ sensing sensors which would not be suitable for such conversion due to large dynamic delay may still be used.

Lambda may be a part of the $NO_x$ sensor. By further noting that the lambda signal has a lag, one may distinguish the present system from other systems on this characteristic, which may use lambda, and may calculate the fresh air flow from lambda directly using known correlations between lambda, air flow, and fuel mass flow. The present system may challenge a use of laggy lambda signals. Laggy signals of an instrument or detector may lag in that they are slow in revealing or indicating a parameter, characteristic, property, or the like being detected, measured, indicated, and/or so forth. Time delays typically encountered when using the lambda in the $NO_x$ sensor may range from 1 to 3 seconds, and the delays may vary depending on the conditions in the exhaust system and may be thus better characterized as intervals of delays or probability of delay values. Furthermore, a lambda sensor signal from an aftertreatment may not necessarily only be delayed but it may simply be almost random during a heavily transient operation. An advantage of the subject lambda is low cost and an easy adaption of the lambda to the inferential determination of EGR mass flow in the present system and approach.

To recap, an inferential exhaust gas recirculation flow detection device may incorporate an exhaust gas recirculation (EGR) valve having a first input, an output and a second input; an exhaust manifold of an engine having an output connected to the first input of the EGR valve and to an input of a turbine, and having an input connected to exhaust ports of cylinders of the engine; an intake manifold of the engine having an input connected to an output of the EGR valve and to an output of a compressor, and an output connected to intake ports of the cylinders; a first pressure sensor situated in the intake manifold; a lambda sensor sensing an oxygen content of an exhaust gas in an exhaust gas flow conveyance between the output of the exhaust manifold and an exhaust output of the device, and having an output of a laggy signal with an indication of the oxygen content; and a processor having an input connected to the first pressure sensor and to the output of the lambda sensor, and having an output connected to the second input of the EGR valve. The processor may calculate one or more rates selected from a group incorporating an estimated EGR mass flow rate and an estimated fresh air mass flow rate;

The processor may calculate the estimated fresh air mass flow rate to the intake manifold from the EGR valve mass flow rate and from a mass conservation law in the system. The lambda sensor may have a delay of the output of the laggy signal providing the indication of oxygen content in the exhaust gas, and a delay of the indication of oxygen content is reduced at least ten times with a use of faster although less accurate calculations of the oxygen content based on models of the EGR valve and the turbine. A varying error of calculations of the oxygen content based on the models of the EGR valve and the turbine may be reduced using the output of the lambda sensor when levels of the laggy signal become stable.

The device may further incorporate a first temperature sensor situated at the intake manifold. The output of the processor may provide a calculated EGR valve mass flow rate based on inputs of a first pressure from the first pressure sensor, a first temperature from the first temperature sensor, estimated properties of the EGR valve, estimated properties of the turbine, and properties of a gas exchange process of the cylinders. The calculated EGR valve mass flow rate may provide a basis to which the EGR valve is controlled by a signal from the output of the processor to the second input of the EGR valve.

The estimated properties of the EGR valve and the estimated properties of the turbine may be continuously affected by a correction from the processor to reduce a steady-state offset between the output of the laggy signal of oxygen content from the lambda sensor and a calculated signal of oxygen content, defined by the estimated properties of the EGR valve and the estimated properties of the turbine.

An EGR valve mass flow may be calculated as a function of a first pressure indicated by the first pressure sensor, and properties of the EGR valve. Properties of the EGR valve may incorporate a valve position that affects a cross section of the EGR valve, and an orifice flow function.

An EGR valve mass flow may be calculated as a mass flow to cylinders minus a mass flow through the turbine plus a fuel mass flow. The mass flow to the cylinders may be expressed as a function of a first pressure at the intake manifold, a first temperature at the intake manifold, and a speed of the engine, and a volumetric efficiency of a cylinder filling process of the cylinders. The mass flow through the turbine may be expressed as a function of a speed of the turbine, and estimated properties of the turbine, and properties of elements at an output of the turbine.

An EGR mass flow may be calculated in a first way and in a second way. Results from the first and second ways may be combined as an average to improve accuracy of the EGR mass flow. In the first way, the EGR mass flow may be calculated as a function of a first pressure at the intake manifold, and properties of the EGR valve. In the second way, the EGR mass flow may be calculated as a mass flow to the cylinders minus a mass flow through the turbine plus a fuel mass flow.

Exhaust gas may be treated by a cascade of one or more aftertreatment devices positioned after the turbine. The lambda sensor may be located between the turbine and an aftertreatment device, between any two aftertreatment devices, or after the cascade.

The lambda sensor may be combined with or contained in an NOx sensor situated in the exhaust gas flow conveyance.

The correction may be based on an interval of a dynamic response of the signal from the lambda sensor. The correction may be avoided or attenuated during a period of time the signal from the lambda sensor is inaccurate.

The laggy signal, indicating oxygen content of an exhaust gas sensed by the lambda sensor, may have a delay of more than a predetermined duration after exposure of the lambda sensor to the exhaust gas. The estimated fresh air flow rate may exhibit a delay less than one tenth of the delay of the laggy signal.

An inferential mechanism for determining a flow of exhaust gas recirculation, may incorporate an exhaust manifold having a first input connected to an exhaust of an engine and having an output; an exhaust gas recirculation (EGR) valve having a first input connected to the output of the exhaust manifold; an intake manifold having an input connected to the output of the EGR valve connected to an output of a compressor, and having an output connected to an input of the engine; a lambda sensor situated between the output of the exhaust manifold and an input of a turbine that is connected to the compressor, or between an output of the turbine and an exhaust output in an ambient environment; a first pressure sensor situated at the intake manifold; and a processor having an input connected to an output of the first pressure sensor and to an output of the lambda sensor, and having an output connected to a second input of the EGR valve.

The lambda sensor may output a signal 0.5 second or longer after exposure to an exhaust gas to detect a content of oxygen in the exhaust gas. The output from the processor connected to the second input of the EGR valve, may provide a signal that controls the EGR valve.

The mechanism may further incorporate a first temperature sensor situated in the intake manifold. The processor may receive, as inputs, pressure indications from the first pressure sensor, temperature indications from the first temperature sensor, and properties of the EGR valve. The processor may process the inputs into a calculated EGR valve flow rate. The processor may provide the signal that controls the EGR valve based on the calculated EGR mass flow rate.

The properties of the EGR valve may incorporate a valve position that affects a cross section of the EGR valve, and an orifice flow function. The signal to the second input of the EGR valve may control the valve position.

A approach for inferring a flow of an exhaust gas recirculation valve, may incorporate detecting a first pressure in an intake manifold connected to an engine; detecting an oxygen content of exhaust gas in an exhaust manifold connected to the engine, with a lambda sensor having a detection to output signal time greater than 0.5 second; and processing the first pressure and the oxygen content into a signal that controls an exhaust gas recirculation (EGR) valve having an input connected to the exhaust manifold and an output connected to the intake manifold.

The signal that controls the EGR valve may be based on an inference of an EGR mass flow calculated from the first pressure in the intake manifold and the oxygen content of the exhaust gas.

Any publication or patent document noted herein is hereby incorporated by reference to the same extent as if each publication or patent document was specifically and individually indicated to be incorporated by reference.

In the present specification, some of the matter may be of a hypothetical or prophetic nature although stated in another manner or tense.

Although the present system and/or approach has been described with respect to at least one illustrative example, many variations and modifications will become apparent to those skilled in the art upon reading the specification. It is therefore the intention that the appended claims be interpreted as broadly as possible in view of the related art to include all such variations and modifications.

What is claimed is:

1. An inferential exhaust gas recirculation flow detection device comprising:
    an exhaust gas recirculation (EGR) valve having a first input, an output and a second input;
    an exhaust manifold of an engine having an output connected to the first input of the EGR valve and to an input of a turbine, and having an input connected to exhaust ports of cylinders of the engine;
    an intake manifold of the engine having an input connected to an output of the EGR valve and to an output of a compressor, and an output connected to intake ports of the cylinders;
    a first pressure sensor and a first temperature sensor situated in the intake manifold;
    a lambda sensor sensing an oxygen content of an exhaust gas in an exhaust gas flow conveyance between the output of the exhaust manifold and an exhaust output of the device, and having an output of a laggy signal with an indication of the sensed oxygen content; and
    a processor having an input connected to the first pressure sensor and to the output of the lambda sensor, and having an output connected to the second input of the EGR valve;
    wherein:
    the processor is configured to determine a calculated EGR valve mass flow rate using a first pressure sensed by the first pressure sensor, a first temperature sensed by the first temperature sensor, estimated properties of the EGR valve, estimated properties of the turbine, and properties of a gas exchange process of the cylinders;
    the processor is configured to calculate an estimated fresh air mass flow rate to the intake manifold from the EGR valve mass flow rate using at least a mass conservation law; and
    the processor uses the calculated EGR valve mass flow rate to control the EGR valve by issuing a signal from the output of the processor to the second input of the EGR valve.

2. The device of claim 1, wherein:
the processor is configured to calculate an estimated oxygen content of the exhaust gas flow using a model of the EGR valve mass flow and a model of the turbine mass flow, wherein the estimated oxygen content of the exhaust gas flow is subject of a varying error; and
the processor is configured to reduce the varying error using the output of the lambda sensor by determining that the laggy signal is stable, and then correcting the varying error using the laggy signal.

3. The device of claim 2, wherein the estimated properties of the EGR valve and the estimated properties of the turbine are continuously affected by a correction from the processor to reduce a steady-state offset between the output of the laggy signal of oxygen content from the lambda sensor and a calculated signal of oxygen content, defined by the estimated properties of the EGR valve and the estimated properties of the turbine.

4. The device of claim 3, wherein:
exhaust gas is treated by a cascade of one or more aftertreatment devices positioned after the turbine; and
the lambda sensor is located between the turbine and an aftertreatment device, between any two aftertreatment devices, or after the cascade.

5. The device of claim 3, wherein:
the correction is based on an interval of a dynamic response of the signal from the lambda sensor; and
the correction is avoided or attenuated during a period of time the signal from the lambda sensor is inaccurate.

6. The device of claim 3, wherein:
the laggy signal, indicating oxygen content of an exhaust gas sensed by the lambda sensor, has a delay of more than a predetermined duration after exposure of the lambda sensor to the exhaust gas; and
the estimated fresh air flow rate exhibits a delay less than one tenth of the delay of the laggy signal.

7. The device of claim 1, wherein: the estimated properties of the EGR valve comprise:
a valve position that affects a cross section of the EGR valve; and
an orifice flow function.

8. The device of claim 1, wherein:
the calculated EGR valve mass flow is calculated as a mass flow to cylinders minus a mass flow through the turbine plus a fuel mass flow;
the mass flow to the cylinders is expressed as a function of a first pressure at the intake manifold, a first temperature at the intake manifold, and a speed of the engine, and a volumetric efficiency of a cylinder filling process of the cylinders; and
the mass flow through the turbine is expressed as a function of a speed of the turbine, and estimated properties of the turbine, and properties of elements at an output of the turbine.

9. The device of claim 1, wherein:
the calculated EGR mass flow is determined as an average of results from the first and second ways of calculating the EGR mass flow;
in the first way, the EGR mass flow is calculated as a function of a first pressure at the intake manifold, and properties of the EGR valve; and
in the second way, the EGR mass flow is calculated as a mass flow to the cylinders minus a mass flow through the turbine plus a fuel mass flow.

10. The device of claim 1, wherein the lambda sensor is combined with or contained in an NOx sensor situated in the exhaust gas flow conveyance.

11. A inferential mechanism for determining a flow of exhaust gas recirculation, comprising:
an exhaust manifold having a first input connected to an exhaust of an engine and having an output;
an exhaust gas recirculation (EGR) valve having a first input connected to the output of the exhaust manifold;
an intake manifold having an input connected to the output of the EGR valve and also connected to an output of a compressor, and having an output connected to an input of the engine;
a lambda sensor situated between the output of the exhaust manifold and an input of a turbine that is connected to the compressor, or between an output of the turbine and an exhaust output in an ambient environment;
a first pressure sensor situated at the intake manifold; and
a processor having an input connected to an output of the first pressure sensor and to an output of the lambda sensor, and having an output connected to a second input of the EGR valve; and wherein:
the lambda sensor outputs a signal 0.5 second or longer after exposure to an exhaust gas to detect a content of oxygen in the exhaust gas;
the output from the processor connected to the second input of the EGR valve, provides a signal that controls the EGR valve;
the processor is configured to determine a calculated EGR valve mass flow rate using on inputs of a first pressure from the first pressure sensor, a first temperature from the first temperature sensor, estimated properties of the EGR valve, estimated properties of the turbine, and properties of a gas exchange process of the cylinders;
the processor is configured to calculate an estimated fresh air mass flow rate to the intake manifold from the EGR valve mass flow rate using at least a mass conservation law; and
the processor uses the calculated EGR valve mass flow rate to control the EGR valve by issuing a signal from the output of the processor to the second input of the EGR valve.

12. The mechanism of claim 11, wherein the properties of the EGR valve comprise:
a valve position that affects a cross section of the EGR valve; and
an orifice flow function.

13. A method for inferring a flow of an exhaust gas recirculation valve, comprising:
detecting a first pressure and a first temperature in an intake manifold connected to an engine;
detecting a measured oxygen content of exhaust gas in an exhaust manifold connected to the engine, with a lambda sensor having a detection to output signal time greater than 0.5 second;
determining estimated properties of an exhaust gas recirculation valve selectively coupling the exhaust manifold to the intake manifold;
determining one or more estimated properties of a turbine coupled to the exhaust manifold to receive exhaust gasses therefrom;
determining a calculated EGR valve mass flow rate using the first pressure, the first temperature, the estimated properties of the EGR valve, the estimated properties of the turbine, and properties of a gas exchange process occurring inside the engine;
calculating an estimated fresh air mass flow rate to the intake manifold from the EGR valve mass flow rate using at least a mass conservation law; and controlling the EGR valve using the calculated EGR valve mass flow rate.

14. The method of claim 13 further comprising:
calculating an estimated oxygen content of the exhaust gas based on the calculated EGR valve mass flow rate;
determining a steady state offset of the estimated oxygen content relative to the measured oxygen content; and
correcting the calculation of the estimated oxygen content using the steady state offset.

* * * * *